(12) United States Patent
Bernard et al.

(10) Patent No.: US 10,796,430 B2
(45) Date of Patent: Oct. 6, 2020

(54) MULTIMODALITY 2D TO 3D IMAGING NAVIGATION (71) Applicant: General Electric Company, Schenectady, NY (US)

(72) Inventors: Sylvain Bernard, Buc (FR); Cynthia Davis, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 129 days.

(21) Appl. No.: 15/960,803

(22) Filed: Apr. 24, 2018

(65) Prior Publication Data

US 2019/0325573 A1 Oct. 24, 2019

(51) Int. Cl.
*G06K 9/00* (2006.01)
*G06T 7/00* (2017.01)
*G06T 11/00* (2006.01)
*G06T 15/08* (2011.01)

(52) U.S. Cl.
CPC .......... *G06T 7/0012* (2013.01); *G06T 11/003* (2013.01); *G06T 15/08* (2013.01); *G06T 2200/04* (2013.01); *G06T 2207/10081* (2013.01); *G06T 2207/10084* (2013.01); *G06T 2207/10088* (2013.01); *G06T 2207/10112* (2013.01); *G06T 2207/30068* (2013.01)

(58) Field of Classification Search
CPC ............................................ G06T 2207/10081
See application file for complete search history.

(56) References Cited

U.S. PATENT DOCUMENTS

| 5,672,877 | A | 9/1997 | Liebig et al. |
|---|---|---|---|
| 7,639,896 | B2 | 12/2009 | Sun et al. |
| 7,738,683 | B2 | 6/2010 | Cahill et al. |
| 7,916,918 | B2 | 3/2011 | Suri et al. |
| 7,945,083 | B2 | 5/2011 | Zhang et al. |
| 8,108,024 | B2 | 1/2012 | Carlsen et al. |
| 8,126,226 | B2 | 2/2012 | Bernard et al. |
| 8,452,613 | B2 | 5/2013 | Meinel et al. |
| 8,527,293 | B2 | 9/2013 | Hammond et al. |
| 8,606,045 | B2 | 12/2013 | Lee |
| 8,644,908 | B2 | 2/2014 | Suri et al. |
| 9,378,550 | B2 | 6/2016 | Twellmann et al. |
| 9,401,047 | B2 | 7/2016 | Bogoni et al. |

(Continued)

OTHER PUBLICATIONS

EP Search Report dated Sep. 18, 2019 from related EP Patent Application No. 19170954.2 (8 pages).

*Primary Examiner* — Oneal R Mistry (57) ABSTRACT

A system and method for the detection of ROIs in images obtained of a breast or other tissue of a patient significantly improves the speed and precision/accuracy of navigation between multimodality 2D and 3D images. In the system and method, images of the tissue are obtained in a DBT acquisition to generate a synthetic 2D image of the imaged tissue and in a 3D, e.g., ultrasound, image acquisition. The 2D image generation process creates a synthetic 2D image that embed a navigation map correlating pixels in the 2D images to sections of the 3D ultrasound volume, such as via a registration between the 3D ultrasound volume and a 3D volume created using the DBT image data. When a synthetic 2D image is reviewed, an ROI on the 2D image is selected and the system will additionally present the user with the section of the 3D volume containing that ROI.

15 Claims, 4 Drawing Sheets

(56) References Cited

U.S. PATENT DOCUMENTS

| | | |
|---|---|---|
| 9,451,924 B2 | 9/2016 | Bernard et al. |
| 9,504,436 B2 | 11/2016 | Suri et al. |
| 9,842,415 B2 | 12/2017 | Bernard et al. |
| 2003/0149364 A1 | 8/2003 | Kapur |
| 2005/0089205 A1 | 4/2005 | Kapur et al. |
| 2006/0136259 A1 | 6/2006 | Weiner et al. |
| 2007/0003118 A1 | 1/2007 | Wheeler et al. |
| 2007/0237372 A1 | 10/2007 | Chen et al. |
| 2008/0242979 A1 | 10/2008 | Fisher et al. |
| 2009/0080765 A1 | 3/2009 | Bernard |
| 2009/0082637 A1 | 3/2009 | Galperin |
| 2010/0076311 A1 | 3/2010 | Tabar et al. |
| 2010/0272338 A1 | 10/2010 | Agnihotri et al. |
| 2011/0087098 A1 | 4/2011 | Fischer et al. |
| 2012/0093383 A1 | 4/2012 | Claus |
| 2012/0114213 A1* | 5/2012 | Buelow ............... G06T 7/344 382/131 |
| 2012/0256920 A1 | 10/2012 | Marshall et al. |
| 2013/0205247 A1* | 8/2013 | Erhard ............... G06F 3/016 715/781 |
| 2013/0211230 A1 | 8/2013 | Sperling |
| 2014/0064580 A1 | 3/2014 | Madabhushi et al. |
| 2014/0082542 A1 | 3/2014 | Zhang et al. |
| 2014/0135623 A1 | 5/2014 | Manak et al. |
| 2014/0219500 A1* | 8/2014 | Moehrle ............ G16H 30/20 382/103 |
| 2016/0133033 A1* | 5/2016 | Highnam ........... G06T 11/005 382/131 |
| 2016/0183901 A1 | 6/2016 | Bernard et al. |
| 2016/0189376 A1 | 6/2016 | Bernard et al. |
| 2017/0011534 A1* | 1/2017 | Costa ............... G06T 11/003 |
| 2018/0033143 A1* | 2/2018 | Buelow ............ A61B 6/025 |
| 2019/0318512 A1* | 10/2019 | Westerhoff ......... G06T 11/008 |

\* cited by examiner

MULTIMODALITY 2D TO 3D IMAGING NAVIGATION

BACKGROUND OF THE DISCLOSURE

The present disclosure relates to the field of combined 2D and 3D imaging and to a method and system for processing 2D and 3D imaging data for improving navigation through the imaging data.

X-ray imaging systems have become a valuable tool in medical applications such as for the diagnosis of many diseases. As standard screening for breast cancer mammography 2-dimensional (2D) x-ray images are taken across the entire breast tissue. These known 2D mammograms are limited by tissue superimposition. That is to say, lesions may be masked by the tissue above or underneath, or normal structures may mimic a lesion. In order to minimize limitations of standard 2D-mammography caused by tissue superimposition, digital breast tomosynthesis using digital receptors has been developed.

Current tomosynthesis systems employ at least one x-ray tube, which is moved, e.g., in an arc, above a stationary detector. In digital breast tomosynthesis (DBT) the volume information of an object of interest can be derived from a series of images, known as projection images or projections, which are taken at various angles by means of one or more x-ray sources. Objects of different heights in a breast display differently in the different projections. From the 2D projection images 3D volumes can be generated for review. The generated 3D volume portions offer advantages to overcome the limitations associated with tissue superimposition.

However, if a potential lesion or other abnormality is identified on a 2D or 3D tomosynthesis X-ray image, a follow-up visit is scheduled for an ultrasound exam or MRI of the breast to confirm or check the initial diagnosis based on the X-ray image. Such rescheduling typically involves a delay of days or even weeks between exams. This amount of time can lead to patient anxiety and concern between the examinations. Further, because the exams are conducted at separate visits, and also because upright positioning and compression is typically used for mammographic X-ray exams and supine positioning is used for ultrasound or prone for MRI, it is very difficult to co-register the X-ray image and ultrasound image such that the radiologist or other practitioner can view the same areas imaged using the different modalities. Present techniques for performing ultrasound examinations of the breast have additional drawbacks, such as the time associated with such examinations.

In addition if the patient is found to have dense breasts she may be referred for whole breast ultrasound screening to be performed on the same visit or subsequent visit. The ultrasound imaging can be performed either by hand by an experienced sonographer technologist and a standard ultrasound imaging system or with a specially designed automated breast ultrasound system (ABUS).

To address this issue with regard to the need for tomosynthesis and 3D ultrasound imaging of the breast, combined imaging systems have been developed such as that disclosed in US Patent Application Publication No. US2014/0135623 entitled SYSTEMS AND METHODS FOR X-RAY AND ULTRASOUND IMAGING, the entirety of which is expressly incorporated herein by reference for all purposes. In these systems, an imaging system including X-ray and ultrasound modalities can be articulated to position and/or compress an object, such as a portion of a human anatomy (e.g., a breast) to perform an X-ray scan or exam. Using information obtained via the X-ray scan or exam, one or more portions of interest of the object may be identified for further analysis using ultrasound imaging on the same system.

While combined imaging systems of this type facilitate the obtaining and review of combined 2D and 3D images of the tissue, in order to effectively review the images, the images are displayed separately to the radiologist or other practitioner. During review of the images, the radiologist will typically separately view the 2D mammography and 3D ultrasound images for one patient, and search for suspicious areas in both images. Radiologists very often need to verify on mammography images suspicious areas of regions of interest (ROI's) found in ultrasound and vice versa. Because the patient or breast positioning used in acquiring mammograms and 3D ultrasound are often very different, it is not immediately obvious to the radiologist what location in an image of one modality corresponds to an ROI found in another modality. In practice, the manual method practiced by radiologists is quite tedious and prone to error. For example, the radiologist will measure the distance of an ROI from the nipple and estimate the clock face position of the ROI on the mammogram and then find the corresponding ROI on the 3D breast ultrasound images based on that measurement.

In order to address this issue and attempt to speed up the workflow of the review of the combined images, one solution that has been developed is disclosed in US Patent Application Publication No. US2014/0082542 entitled VIEWING AND CORRELATING BETWEEN BREAST ULTRASOUND AND MAMMOGRAM OR BREAST TOMOSYNTHESIS IMAGES, the entirety of which is expressly incorporated herein by reference for all purposes. In this solution, mammography images, that is, images taken along the mediolateral-oblique (MLO) and cranial-caudal (CC) planes, and a 3D ultrasound image are each obtained of the tissue being imaged. In response to the selection of an identified ROI on one of the mammogram images or ultrasound images by the user of the system, the system automatically calculates the coordinates of the selected ROI within the other modality image(s) and provides navigation aids on those image(s) to assist the user in determining the location of the ROI on the other of the images.

However, variations in the images obtained in the mammography and ultrasound modalities, along with any variations in the form or state of the tissue being imaged, such as the upright compression of the breast during the mammography imaging versus the supine compressed tissue in ultrasound imaging, creates significant correlation issues between the locations of the selected ROIs within the mammography images and within the ultrasound images. Further the separate review of the image data of each modality greatly slows down the review and workflow. This, in turn, presents significant problems with the proper determination of the exact location of the ROI in either image, particularly with regard to small ROIs and/or when the images are obtained at different times and with separate compressions, thereby increasing the time required to properly analyze the images and increasing the number of false positive screening callbacks and eventually biopsies.

Accordingly, it is desirable to develop a system and method for the creation of a navigation map utilizing 2D image data obtained from a tomosynthesis acquisition for the identification and location of ROIs in a 3D ultrasound volume that improves upon the state of the art.

BRIEF DESCRIPTION OF THE DISCLOSURE

There is a need or desire for a system and method for the detection of ROIs in images obtained of a breast or other tissue of a patient significantly improves the speed and accuracy of navigation between multimodality 2D and 3D images. In the system and method, images of the tissue are obtained in a 3D DBT acquisition to generate a synthetic 2D image of the imaged tissue and in a 3D, e.g., ultrasound or MRI, image acquisition. The 2D image generation process creates a synthetic 2D image that each embed a navigation map correlating pixels in the 2D image to sections of the 3D ultrasound volume, such as via a registration between the 3D ultrasound volume and a 3D DBT volume created using the DBT image data. When a synthetic 2D image is reviewed, an ROI on the 2D image is selected and the system will additionally present the user with the section of the 3D volume containing that ROI. With the use of synthetic 2D DBT images, as opposed to the 2D images presented to the radiologist can more closely approximate the locations of the ROIs within the planes of the 3D volume, greatly enhancing the speed and precision of navigation to the ROIs between planes of the imaging modalities.

According to another exemplary aspect of the disclosure, the synthetic 2D image can be enhanced using results of a computer-aided detection (CAD) system applied to the 3D images to define the locations of the ROIs in the 2D synthetic image. The enhanced 2D image can then be presented with the ROI locations to make navigation to those ROIs in the 3D image(s) more efficient.

According to another exemplary aspect of the disclosure, a system for assisting a user in navigating through 2D and 3D image data to locate a region of interest within a breast tissue includes a 2D image acquisition system for acquiring 2D image data, a 3D image acquisition system for acquiring 3D image data, an analysis module operably connected to the 2D image acquisition system and the 3D image acquisition system and configured to generate a synthetic 2D image and a 3D volume from the acquired 2D image data, to generate a 3D volume from the 3D image data, to correlate locations within the 3D image volume to locations within the 3D image volume, to generate a navigation map providing information for each pixel in the synthetic 2D image corresponding to a plane in the 3D volume and the 3D volume and to select and present a section within the 3D volume corresponding to the navigation map information for a pixel selected within the synthetic 2D image, a display operably connected to the analysis module and operable to display the synthetic 2D image and sections of the 3D volume and an input operably connected to the analysis module and configured to receive commands from a user regarding the selection of a pixel within the synthetic 2D image present on the display.

According to still another aspect of the disclosure, a method of navigating between images of an object obtained in different imaging modalities of the object, include the steps of obtaining a number of x-ray images of the object at varying angles relative to the object in a digital tomosynthesis acquisition, obtaining a three-dimensional (3D) volumetric image of the object in a 3D imaging acquisition, forming a DBT volume of the object from the x-ray images, forming a synthetic two-dimensional (2D) image of the object from the x-ray images and/or the DBT volume, forming a navigation map correlating pixels of the synthetic 2D image with associated planes in the DBT volume, correlating the 3D volumetric image from the 3D imaging acquisition with the DBT volume from the digital tomosynthesis acquisition, displaying the synthetic 2D image; and displaying a section of the 3D volumetric image corresponding to a location of a pixel in the synthetic 2D image in response to a selection of the pixel in the displayed synthetic 2D image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrases "image" or "reconstructing an image" are not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Systems formed in accordance with various embodiments provide an imaging system including a 2D imaging modality (i.e., X-ray imaging) and a 3D imaging modality (e.g., ultrasound (US) or magnetic resonance imaging (MRI)) for performing scans on the object or patient using both modalities to enhance the scan results and diagnosis.

Some embodiments provide an imaging system having a modified compression paddle that includes and/or accepts a cassette containing an ultrasound probe that can be moved to various locations within the field of view of the imaging system. For example, a control module utilizing appropriately configured software may obtain multiple X-ray images and an ultrasound scan to identify potential regions of interest, such as potential lesions, for further investigation. In some embodiments, a cassette containing an ultrasound probe may be positioned between a compression plate and an X-ray detector.

Some exemplary embodiments provide for improved co-registration of X-ray and ultrasound images, for example by acquiring such images at substantially the same time and/or by acquiring such images utilizing a same or similar amount of compression.

A technical effect of at least one embodiment includes reduced time required to acquire and analyze results of combined mammographic exams, including 2D imaging and 3D imaging exams. A technical effect of at least one embodiment includes reducing errors associated with multimodal imaging examinations. A technical effect of at least one embodiment includes improved co-registration of X-ray and ultrasound images, thereby improving and speeding up navigation between 2D and 3D images during review of the images, consequently improving diagnoses and/or reducing time and skill required by a medical professional for analysis of acquired images.

Figure 1:
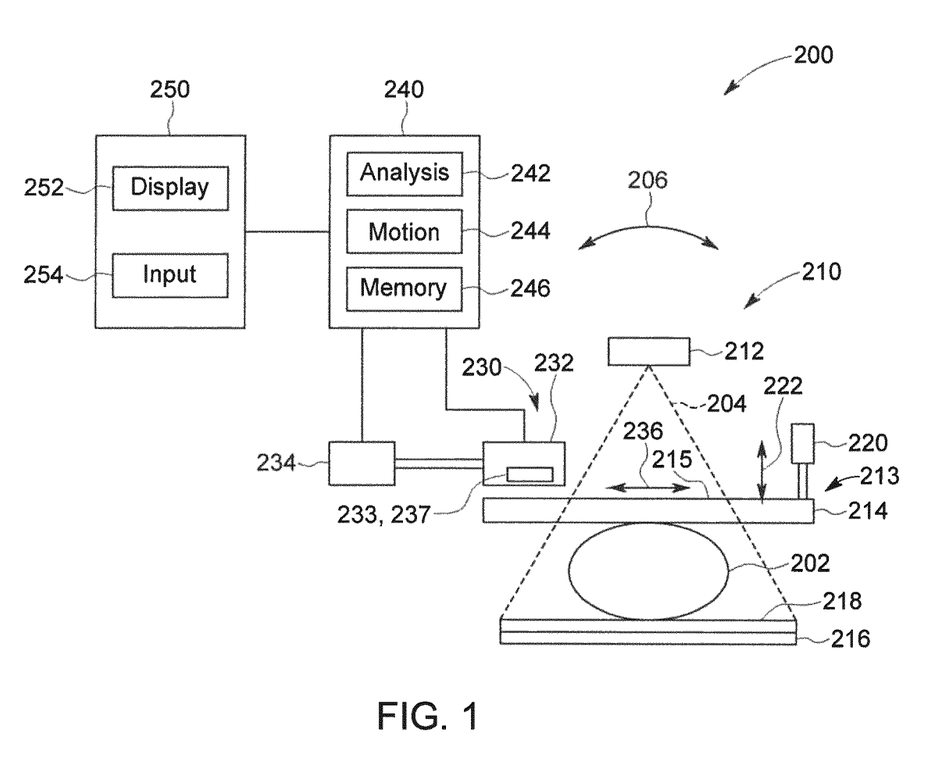
FIG. 1 is a schematic view of a multimodal imaging assembly according to an exemplary non-limiting embodiment of the disclosure.

FIG. 1 provides an example of an imaging system 200 for imaging an object in accordance with an exemplary embodiment, such as that disclosed in US Patent Application Publication No. 2014/0135623, entitled SYSTEMS AND METHODS FOR X-RAY AND ULTRASOUND IMAGING, which is expressly incorporated herein by reference in its entirety for all purposes. In the illustrated embodiment, the system 200 and associated method may employ structures or aspects of various embodiments discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

In the system and method, an object 202 is positioned between plates of an imaging system. For example, the object may be a portion of human anatomy such as a breast. Because X-ray scans effectively view an object in two dimensions (2D), structures such as breast tissue that exceed a certain density and/or thickness may not be readily amenable to X-ray scans. Compression may be used to render a breast more amenable to X-ray imaging. For example, compression may reduce the thickness of the breast, and stretch tissue to a wider viewing area in two dimensions, allowing for improved identification of structures located during a scan. Further, by presenting a thinner overall structure to an X-ray detecting system, the X-ray dosage required to image the breast may be reduced.

The exemplary illustrated embodiment of FIG. 1 presents a schematic view of an imaging system 200 formed in accordance with various embodiments. The imaging system 200 is configured to provide both 2D (i.e., X-ray) and 3D (e.g., ultrasound or MRI or contrast-enhanced DBT, or CT) imaging modalities that may be used to perform scans on an object (e.g. a patient) in the same visit to a scanning location. For example, the imaging system 200 may be used to perform an X-ray scan and an ultrasound scan substantially consecutively. Substantially consecutively may be understood to describe, for example, scans that are performed with a relatively short time interval therebetween. In some embodiments, the 2D scan and the 3D scan may be performed substantially consecutively with a time interval of less than about 5 seconds therebetween. In some embodiments, the 2D scan and the 3D scan may be performed substantially consecutively with a time interval of less than about 10 seconds therebetween. In some embodiments, the 2D scan and the 3D scan may be performed substantially consecutively with a time interval of less than about 1 minute therebetween. In some embodiments, the 2D scan and the 3D scan may be performed substantially consecutively with a time interval of less than about 5 minutes therebetween. However, it should be appreciated that other time intervals are contemplated as well and that the imaging system 200 can be formed with separate devices for performing the 2D scan and 3D scan at different times and/or at different locations.

The imaging system 200 may be used to image an object, such as a human breast 202. The imaging system 200 may be articulable with respect to the object being imaged. In the illustrated embodiments, the imaging system 200 is articulable in a rotational direction 206 and thus may be used to view the breast 202 from a variety of angles for different scans. For example, a first X-ray scan may be performed at a first angle, and a second X-ray scan may be performed at a second angle to provide a different view of the breast 202. Because the breast 202 is a three-dimensional (3D) object and the X-ray scan effectively sees the breast 202 in two dimensions, a structure within the breast 202 may be obscured, blocked, or otherwise un-identifiable at one angle or view, but may be identifiable when viewed at a different angle or view. Thus, improved identification of structures within the breast 202 may be achieved by performing X-ray scans at two or more different angles or views.

In the illustrated embodiment, the system 200 is configured to obtain a 3-dimensional X-ray image, such as via 3D digital breast tomosynthesis (DBT). In some embodiments, tomosynthesis imaging information may be acquired utilizing a tube or other structure that may rotate between about 10 and 30 degrees in one or more directions to provide a volumetric image. In some embodiments, the amount of compression applied between plates or paddles may be reduced (e.g., in connection with the use of 3D DBT). For example, an amount of compression that is sufficient to position the object (e.g., breast) may be used. Thus, in various embodiments, various imaging techniques may be employed. Further, various mountings of an X-ray detection unit proximate to a plate or paddle may be employed (e.g., stationary or rotational).

The imaging system 200 includes a 2D imaging or X-ray module 210, a 3D imaging module 230, such as an ultrasound or MRI module, a control module 240, and an interface 250. Generally speaking, in the illustrated embodiment, the X-ray module 210 is configured to perform an X-ray scan of the object 202 at various angles with respect to the object 202, such as in a DBT scan, and to provide X-ray imaging information to the control module 240. The control module 240 is also configured to control the 3D imaging module 230 to perform a scan of the object 202 to facilitate improved analysis and/or diagnosis of the object 202 and/or one or more regions of interest within the object 202. For example, the 3D imaging scan may be used to confirm whether or not one or more regions of interest were false positives in the X-ray scan (e.g., not a cause for concern) or whether not one or more regions of interest appear to be of medical interest (e.g., potentially cancerous).

In the illustrated exemplary embodiment, the X-ray module 210 includes an X-ray source 212, a paddle assembly 213 (including an upper plate 214 and a lower plate 216), a detector 218, and an actuator 220. The X-ray source 212 is configured to emit X-rays that pass through an object (e.g., object 202) and are received by the detector 218. The detector is position on, mounted to, and/or forms a part of the lower plate 216. Information acquired by the detector 218 is communicated to the control module 240. The X-ray source 212 in the illustrated embodiment has a field of view 204 that projects on to the detector 218.

The paddle assembly 213 includes an upper plate 214 and lower plate 216. The upper plate 214 and lower plate 216 are an example of first and second opposed plates that are articulable with respect to each other. In the illustrated embodiment, the lower plate 216 is fixed and the upper plate 214 is articulable along a compression direction 222 by the actuator 220. The upper plate 214 may be articulated downward (in the sense of FIG. 2) toward the lower plate 216 to compress the breast and upward away from the lower plate 216 to reduce an amount of compression on the breast 202 and/or to release the breast 202 from between the upper plate 214 and the lower plate 216. In alternate embodiments, other arrangements may be employed to provide articulation of two plates with respect to each other. In the illustrated embodiment, the upper plate 214 and the lower plate 216 are depicted as substantially flat. In alternate embodiments, plates may be employed having curved or otherwise contoured profiles. Other types or orientations of articulation may be employed as well. As one example, in some embodiments, the first and second plates may be coupled by a pivot and thus be rotatable with respect to each other. The actuator 220 may be controlled by the control module 240 and/or an operator. In various embodiments, a variety of devices or mechanisms (e.g., one or more motors, pneumatic or hydraulic cylinders, electronic linear actuators, hand-operated mechanisms, or the like) may be employed to articulate the plates. In some embodiments, one or more paddles or plates may translate and/or rotate on a gantry which may be mounted to a floor and/or a wall.

In various embodiments, the upper plate 214 and/or the lower plate 216 may be configured to reduce any potential attenuation (e.g., radiolucent) of an X-ray as the X-ray passes through the plates. Further, in various embodiments, the upper plate 214 and/or the lower plate 216 may be substantially transparent to provide an operator with visual confirmation of the positioning of the object 202.

The detector 218 is configured to receive X-ray beams that have been emitted from the X-ray source 212 and have passed through the breast 202, and to provide X-ray imaging information to the control module 240. The control module 240 is configured to receive the X-ray image information from the detector 218 and/or to reconstruct 2D and/or 3D X-ray image(s) using the X-ray information from the detector 218. In some embodiments, the detector 218 may include more than one detector, such as an array of detectors. In the illustrated embodiment the detector 218 is mounted to the lower plate 216. In other embodiments, the detector 218 may be a part of, embedded within or otherwise associated with a plate or paddle.

In the illustrated exemplary embodiment, the 3D imaging module is constructed as an ultrasound module 230, such as an automated breast ultrasound system (ABUS), that is configured to acquire ultrasound information of the object to be imaged. In the illustrated embodiment, the ultrasound module 230 includes an ultrasound transducer 232, a dispensing module 233, an actuator 234, and a reservoir 237. The ultrasound transducer 232 is configured to send an ultrasonic beam or beams through a portion of an object and to receive returned ultrasonic beams. Information acquired by the ultrasound transducer is then used to reconstruct a 3D image corresponding to the object, or portion thereof, that is scanned. For example, information from the ultrasound transducer 232 may be communicated to the control module 240 and/or the interface 250 for image reconstruction and/or analysis.

In some embodiments, the ultrasound transducer 232 includes an array of aligned transducers that are configured to be articulated in a substantially lateral direction, allowing for a region of interest of the breast to be ultrasonically scanned in a single pass. The ultrasound transducer 232 may be part of a cassette type assembly that is movable within and/or along a plate or paddle (as one example, an upper surface 215 of the upper plate 214, or, as another example, a lower surface of the lower plate 216). A liquid or gel may be employed to create or improve an acoustic contact between the ultrasound probe and a casing or surface of the plate or paddle.

The actuator 234 is configured to articulate the ultrasound transducer 232 to a desired position for scanning the object 202 or a region of interest of the object (e.g., a region of interest of the breast 202). The actuator 234 may position the ultrasound transducer based on control signals or messages received from the control module 240. In the illustrated embodiment, the actuator 234 is configured to articulate the ultrasound transducer 232 in an ultrasound direction 236 substantially laterally along an upper surface 215 of the upper plate 214. In various embodiments, the actuator 234 may include one or more of a variety of devices or mechanisms (e.g., one or more motors, pneumatic or hydraulic cylinders, electronic linear actuators, or the like).

The ultrasound transducer 232 may be positioned outside of the field of view 204 of the X-ray source 212 while an X-ray scan is being performed. After the X-ray scan is complete and a region of interest has been selected, the actuator 234 may position the ultrasound transducer 232 to scan the object 202. Thus, the ultrasound transducer 232 may be articulable between a position outside of the field of view 204 and one or more positions inside of the field of view 204. In some embodiments, the ultrasound transducer may be mounted to one or more paddles and plates, and articulable across one or more surfaces, for example, via a track or guide. In some embodiments, the ultrasound transducer may be movable in a plurality of lateral directions (e.g., the actuator 234 may include a plurality of linear actuators or otherwise be configured to articulate the ultrasound transducer 232 in a plurality of directions). For example, the actuator 234 may be configured to move the ultrasound transducer in a raster pattern sized and configured to cover a region of interest. Further still, in some embodiments, the ultrasound transducer 232 may be removably mounted to a paddle or plate, and physically removed from the paddle or plate during X-ray scanning.

The dispensing module 233 in the illustrated exemplary embodiment illustrated in FIG. 1 includes a reservoir 237 (e.g., a sealed reservoir). The dispensing module 233 is configured to dispense a liquid or gel from the reservoir 237 to acoustically couple an ultrasound transducer with a surface of a plate or paddle. For example, in the illustrated embodiment, the dispensing module 233 is configured to dispense a liquid to the upper surface 215 of the upper plate 214 over which the ultrasound transducer 232 traverses during ultrasound scanning of one or more regions of interest. The liquid or gel is configured to improve the acoustic contact between a transducer and a plate or paddle, so that soundwaves may be transmitted between the transducer and the object via the plate or paddle (e.g., with the plate or paddle pressed against the object to be scanned as the object is compressed). In some embodiments, a portion of the dispensing module and/or a surface of a plate or paddle may be configured to improve retention of liquid or gel on the surface when the imaging system 200 is articulated in the rotational direction 206 at an angle in which gravity may urge the liquid or gel off of the surface.

The control module 240 includes a motion control module 244 that is configured to control movement and/or position of the X-ray source 212, the plates 214, 216 and/or the ultrasound transducer 232 to scan the object 202 and/or a region of interest within the object 202.

The analysis module 242 of control module 240 is configured to receive information from the detector 218 of the X-ray module 210 and the ultrasound transducer 232, and to reconstruct 2D and 3D images using the information using each image data set. The analysis module 242 may also be configured, for example, to adjust or account for compression when reconstructing an image using ultrasound information from the ultrasound transducer 232. In some embodiments, reconstructed X-ray and/or ultrasound images may be provided by the control module to a practitioner or other system via the display 252 on the interface 250.

In the illustrated embodiments, the analysis module 242 may include or have access to software, such as a computer-aided detection (CAD) system, that facilitates the identification of lesions or other regions of interest in a 2D image(s) and/or the 3D images provided by the X-ray and ultrasound scans. In some embodiments, the control module 240 may receive an input from a practitioner, such as through the interface 250, identifying one or more regions of interest. For example, in some embodiments, the analysis module 242 is configured to autonomously identify one or more potential lesions or other aspects of interest based on X-ray information received from the detector 218. In some embodiments, the region or regions of interest may be identified by a practitioner based on an analysis of one or more of the 2D and/or 3D images on the display 252.

The interface 250 is configured to allow information and/or commands to be communicated between the control module 240 and a practitioner. In the illustrated embodiments, the interface 250 includes a display module 252 and an input module 254. The display module 252 may include, for example, a printer, a screen, a touchscreen, a speaker, or the like. The input module 254 may include a touchscreen (e.g., a touchscreen shared between the display module 252 and the input module 254), a mouse, stylus, keyboard, keypad, or the like. One or more reconstructed images may be displayed via the display module 252.

The input module 254 is configured to receive input from a practitioner to perform one or more imaging activities. For example, the input module 254 may receive input from a practitioner establishing one or more settings or parameters for imaging. Further, the input module 254 may receive input from a practitioner establishing a region of interest within the images for further evaluation or display.

In one exemplary embodiment of the system 200, after the 2D and 3D imaging scans of the object 202 have been performed, the analysis module 242 will generate synthetic 2D image(s) and 3D images/volumes of the object 202 from the X-ray/DBT/full filed digital mammography (FFDM)/contrast-enhanced spectral mammography (CESM) scans performed by the X-ray source 212 and the data provided by the X-ray detector 218 to the analysis module 242. An exemplary embodiment of a DBT/DBT-FFDM/DBT-CESM imaging process performed on the image data from the X-ray detector 218 is disclosed in U.S. Pat. No. 8,126,226, entitled SYSTEM AND METHOD TO GENERATE A SELECTED VISUALIZATION OF A RADIOLOGICAL IMAGE OF AN IMAGED SUBJECT, and in US Patent Application Publication No. US2016/0189376, entitled METHOD AND SYSTEM FOR OBTAINING LOW DOSE TOMOSYNTHESIS AND MATERIAL DECOMPOSITION IMAGES, the entirety of which are each expressly incorporated by reference herein for all purposes. In addition, the analysis module 242 can employ the images from the ultrasound transducer 232 to generate a 3D volume of the object 202.

In another exemplary embodiment, the system and method for acquiring and processing 2D and 3D imaging data for improving navigation through the imaging data may include the acquisition of 2D and 3D imaging data from a separate and independent DBT X-ray imaging system and a separate and independent ABUS ultrasound imaging system.

Figure 2:
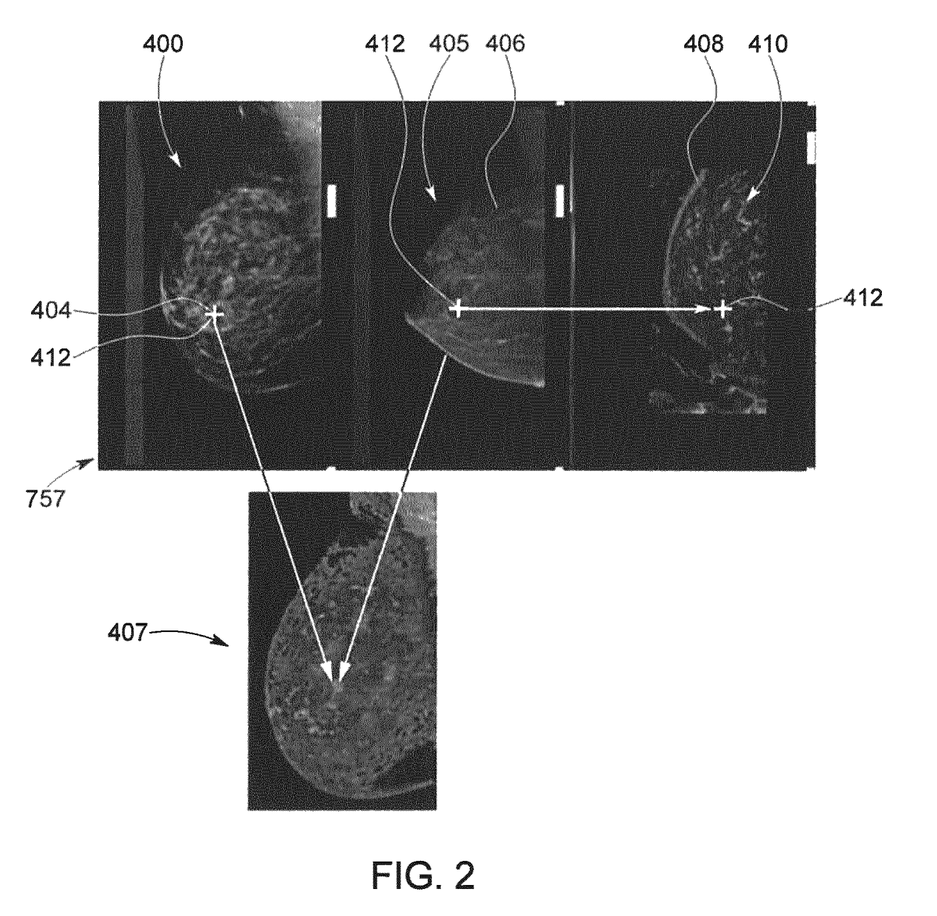
FIG. 2 is a schematic view of the simultaneous display of a synthetic 2D image, a 3D plane and a 3D section for a selected pixel of the synthetic 2D image correlated via a navigation map according to an exemplary non-limiting embodiment of the invention.

Looking now at FIG. 2, in generating both the synthetic 2D image(s) and 3D volume(s) containing a number of planar views of the imaged tissue from the DBT acquisition or scan, the analysis module 242 maps location of any point on the synthetic 2D image 400 to the location of a voxel within the generated 3D DBT volume 405. As such, for any synthetic 2D image 400 presented to the user on the display 252, the analysis module 242 creates an associated but hidden navigation map 402 for the image 400 containing the height or z-axis information for any (x,y) pixel 404 on the synthetic 2D image 400. The z-axis information associated with each (x,y) pixel 404 is correlated by the analysis module 242 to the corresponding z-axis plane 406 of the 3D DBT volume 405. This process is described in U.S. Pat. No. 8,126,226 along with U.S. Pat. No. 9,842,415.

Further, with the information on the z-axis plane 406 in the 3D DBT volume 405, the analysis module 242 can correlate the (x,y,z) location in the DBT z-axis plane 406 to a corresponding section or plane 408 of the automated breast ultrasound system (ABUS) or MRI 3D or CEDBT or CT volume 410. The DBT plane 406 to ABUS/MRI/CEDBT/CT plane or section 408 correspondence can require a quite straightforward transformation when the image modalities were obtained at the same time and/or with the object 202 in the same position and/or compression in the system 200, though some resolution scaling may need to be performed.

Alternatively, the DBT plane 406 to ABUS/MRI/CEDBT/CT section 408 correspondence can require their positions in the respective 3D volumes 405,410 to be correlated using a suitable transformation to accommodate for the changes in position of the object/tissue 202 (e.g., compression of the object/tissue 202) between imaging modalities. The registration process could rely on matching findings detected in the DBT volume 405 and ABUS/MRI/CEDBT/CT volume 410, such as for example, by utilizing finite element model in a known manner, and/or by employing a linear affine transformation-MLO translation utilizing the compression angle from the dicom header from the ABUS images. For registration or translation of the DBT volume 405 to an MRI/CT volume 410, the lack of compression performed in the MRI/CT scan enables finite element modeling to be effectively utilized to transform the MRI/CT scan volume 410 to register it to the DBT volume 405.

With this mapping of the pixels 404 in the synthetic 2D DBT image 400 to the DBT volume 405, and the corresponding correlation and/or registration of the DBT volume 405 to the 3D imaging (ABUS or MRI or CEDBT or CT) volume 410, in the review of the synthetic 2D image 400 on the display 252 by the radiologist, the selection of an (x,y) pixel 404 corresponding to a potential region of interest within the synthetic 2D image 400 being reviewed allows the analysis module 242 to access and read the navigation map 402 to determine the z-axis information for that pixel 404. In a particular embodiment, the analysis module 242 can then automatically utilize the z-axis information for the pixel 404 selected to locate the corresponding DBT plane 406 and the ABUS/MRI/CEDBT/CT section 408 registered with that DBT plane 406, which, e.g., can be an axial or coronal plane/view of the ABUS volume 410 created in a process disclosed in US Patent Application Publication No. US20100076311, entitled THICK SLICE PROCESSING AND DISPLAY OF INFORMATION FROM A VOLUMETRIC ULTRASOUND SCAN OF A CHESTWARDLY COMPRESSED BREAST, which is expressly incorporated by reference herein in its entirety for all purposes. The analysis module 242 can then present the ABUS/MRI section 408, and optionally the DBT plane 406, on the display 252 in conjunction with the synthetic 2D image 400 with a cross or cursor 412 on each image 400,406,408 indicating the corresponding precise position of the pixel 404 selected in the image 400. As a result the speed of navigation between the DBT and ABUS/MRICEDBT/CT image data sets/volumes is greatly enhanced, consequently speeding up the overall workflow when reading DBT and ABUS/MRI/CEDBT/CT volumes 405, 410 obtained in a combined image acquisition.

Figure 3:
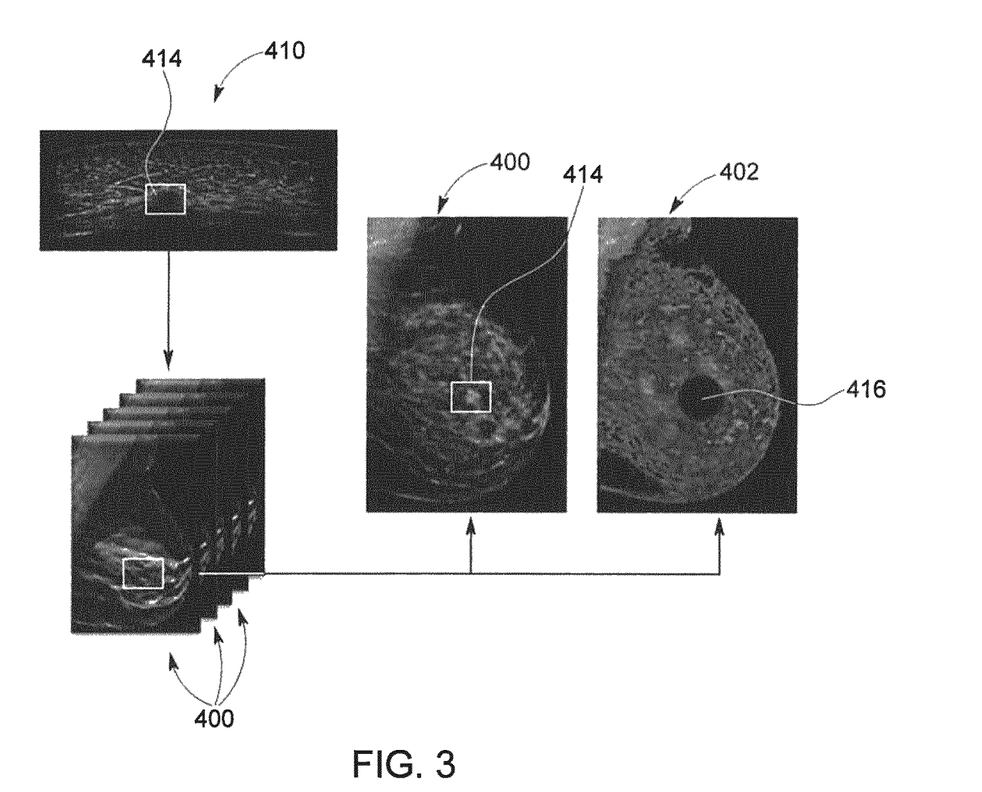
FIG. 3 is a schematic view of an identified region of interest from a 3D volume used to improve a correlated synthetic 2D image and navigation map according to an exemplary non-limiting embodiment of the invention.

Referring now to FIG. 3, in another exemplary embodiment of the disclosure the analysis module 242 can be utilized to identify volumes of interest (VOIs) or regions of interest (ROIs) 414 in the ABUS/MRI/CEDBT/CT volume 410. This identification of the VOIs/ROIs 414 can be performed manually by the user through the interface input 254 during a review of the ABUS/MRI/CEDBT/CT volume 410, or can be performed automatically using a computer aided detection (CAD) system 413 associated with the analysis module 242. As certain ROIs 414 are more readily detectable/visible in the ABUS volume 410 than in the DBT volume 405, the identification of the ROIs 414 in the ABUS/MRI/CEDBT/CT volume 410 can be used to mitigate both the omission of the ROIs 414 in the DBT volume 405 and the rate of false positives where the ROI 414 is present in the ABUS/MRI/CEDBT/CT volume 410 but not in the DBT volume 405.

Once identified in the ABUS/MRI/CEDBT/CT volume 410, the correlation of the ABUS/MRI/CEDBT/CT volume 410 to the DBT volume 405 allows for the locations of the ROIs 414 to be translated into the DBT volume 405 where the ROIs 414 can be represented in the synthetic 2D image 400 generated by the analysis module 242 using a reprojection operation. Additionally, in other exemplary embodiments the representation of the VOI/ROI 414 in the synthetic 2D image 400 can include a boundary for the VOI/ROI 414 overlaid within the synthetic 2D image 400. Optionally, the ROI/VOI 414 as obtained from the DBT volume 405 can also be blended onto the existing synthetic 2D image 400. Alternatively, the synthetic image DBT images 400 are enhanced/enriched during the generation process for the synthetic 2D image 400, such as that disclosed in U.S. Pat. No. 9,842,415, entitled METHOD FOR PROCESSING TOMOSYNTHESIS ACQUISITIONS IN ORDER TO OBTAIN A REPRESENTATION OF THE CONTENTS OF AN ORGAN, and/or in US Patent Application Publication No. US2016/0183901, entitled METHOD AND SYSTEM FOR TOMOSYNTHESIS PROJECTION IMAGES ENHANCEMENT, which are each expressly incorporated herein by reference in their entirety for all purposes, to take the ROIs 414 position into account and avoid non-relevant overlapping tissues within the presented image 400.

Figure 4:
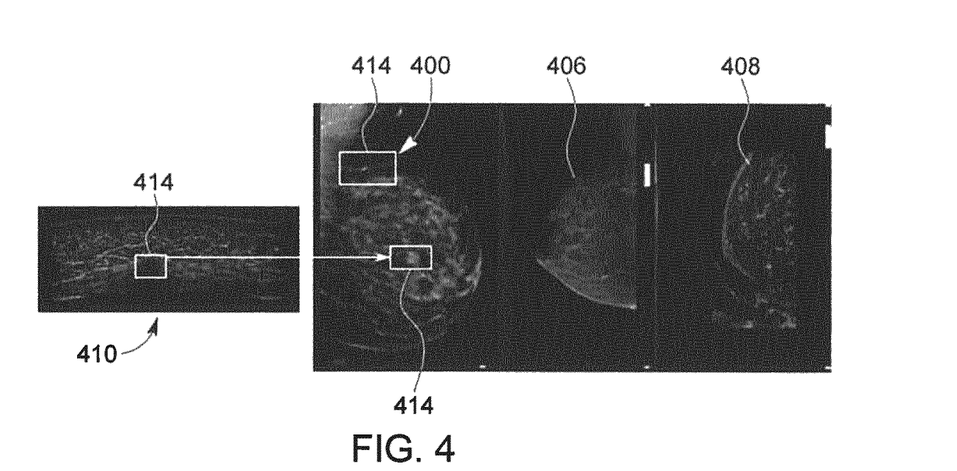
FIG. 4 is a schematic view of the display of the synthetic 2D image and overlaid region of interest identified in the 3D volume of FIG. 3, according to an exemplary non-limiting embodiment of the invention.

In addition, the navigation map 402 can be modified accordingly to direct the user upon the selection of pixels 404 within the modified area 416 of the map 402 to the corresponding ABUS/MRICEDBT/CT section 408 including the VOI/ROI 414, thereby providing more efficient synthetic 2D to DBT/ABUS/MRI/CEDBT/CT navigation. In particular, with reference to the exemplary embodiment illustrated in FIG. 4, with the ability to represent the VOIs/ROIs 414 overlaid in the synthetic 2D image 400 that are manually identified or identified using the CAD system 413 in the ABUS/MRI/CEDBT/CT volume 410. The selection of a VOI/ROI 414 represented on the synthetic 2D image 400 instructs the analysis module 242 to present the corresponding DBT plane 406 and/or ABUS/MRI/CEDBT/CT plane/section 408 on the display 252 for a side-by-side comparison of the planes of interest carrying the multi-modality information on the selected VO/ROI 414.

Figure 5:
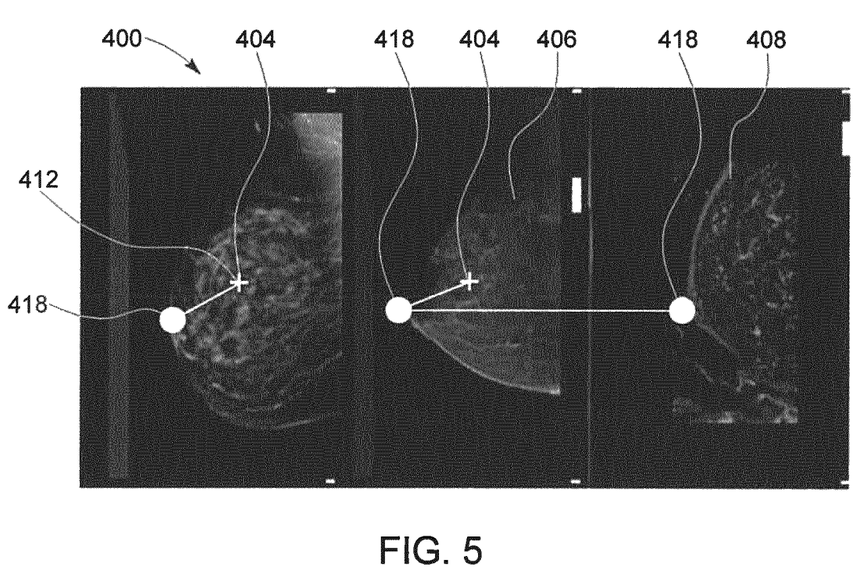
FIG. 5 is a schematic view of the simultaneous display of a synthetic 2D image, a 3D plane and a 3D section along with selected pixel and a nipple position correlated via a navigation map according to an exemplary non-limiting embodiment of the invention.

Looking now at FIG. 5, in addition to the ROIs 414 that are identified in the ABUS/MRI volume 410 and correlated into the synthetic 2D image 400 and DBT volume 405, the position of the nipple 418 is represented in the ABUS/MRI volume 410 with high precision, but is not readily apparent in the synthetic 2D image 400 or 3D volume 405. Thus, with the correlation or registration of the ABUS/MRI volume 410 to the DBT volume 405 and synthetic 2D image 400, the position of the nipple 418 can be represented/re-projected onto the synthetic 2D image 400 and the 3D volume 405. When a pixel 404 representing an ROI 414 on the synthetic 2D image 400 is selected on the display 252 by the user, the nipple position 418 can be presented on the synthetic 2D image(s) 400, the DBT plane 406 (if presented) and optionally on the ABUS/MRI section 410 corresponding to the information contained within the navigation map 402 associated with the pixel 404. In addition, the images 400, 406 and 410 can include the distance of the VOI/ROI 414 to the nipple 418, a clockwise position of the VOI/ROI 414 with respect to the nipple 418 and the distance of the VOI/ROI 414 from the skin line 420. This information is reported for further treatment wherein VOI/ROI 414 localization in the anatomy is required as biopsy.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of navigating between images of an object obtained in different imaging modalities of the object, the method comprising:
obtaining a number of x-ray images of the object at varying angles relative to the object in a digital breast tomosynthesis (DBT) acquisition;
obtaining a three-dimensional (3D) volumetric image of the object in a 3D imaging acquisition;
forming a DBT volume of the object from the x-ray images;
forming a synthetic two-dimensional (2D) image of the object from the x-ray images and/or the DBT volume;
forming a navigation map correlating pixels of the synthetic 2D image with associated planes in the DBT volume;
correlating the 3D volumetric image from the 3D imaging acquisition with the DBT volume from the DBT acquisition;
displaying the synthetic 2D image; and
displaying a section of the 3D volumetric image corresponding to a location of a pixel in the synthetic 2D image in response to a selection of the pixel in the displayed synthetic 2D image,
wherein the step of forming the synthetic 2D image further comprises the steps of:
detecting one or more volumes of interest (VOIs) within the 3D volumetric image;
determining the positions of the one or more VOIs from the 3D volumetric image within the DBT volume;
reprojecting the VOIs from the DBT volume; and
modifying the navigation map to include the location of the VOIs.

2. A method according to claim 1 wherein the step of obtaining a number of x-ray images of the object and the step of obtaining a 3D volumetric image of the object occur with the object in the same position.

3. A method according to claim 1 wherein the step of forming the navigation map comprises associating a height value to each pixel of the synthetic 2D image corresponding to a position in the 3D volumetric image.

4. A method according to claim 1 wherein the VOI reprojections are blended onto the synthetic 2D image after formation of the synthetic 2D image.

5. A method according to claim 1 wherein the VOI reprojections are utilized to enrich the synthetic 2D image during formation of the synthetic 2D image.

6. A method according to claim 1 further comprising the step of representing a boundary overlay of the VOI from the DBT volume within the synthetic 2D image.

7. A method of navigating between images of an object obtained in different imaging modalities of the object, the method comprising:
obtaining a number of x-ray images of the object at varying angles relative to the object in a digital breast tomosynthesis (DBT) acquisition;
obtaining a three-dimensional (3D) volumetric image of the object in a 3D imaging acquisition;
forming a DBT volume of the object from the x-ray images;
forming a synthetic two-dimensional (2D) image of the object from the x-ray images and/or the DBT volume;
forming a navigation map correlating pixels of the synthetic 2D image with associated planes in the DBT volume;
correlating the 3D volumetric image from the 3D imaging acquisition with the DBT volume from the DBT acquisition;
displaying the synthetic 2D image; and
displaying a section of the 3D volumetric image corresponding to a location of a pixel in the synthetic 2D image in response to a selection of the pixel in the displayed synthetic 2D image, further comprising the steps of:
detecting a position of the nipple within the 3D volumetric image;
locating the position of the nipple from the 3D volumetric image into the DBT volume; and
representing the nipple in the synthetic 2D image.

8. A method according to claim 7 wherein the step of representing the nipple in the synthetic 2D image includes representing a distance from a selected pixel in the synthetic 2D image to the nipple.

9. A method according to claim 7 wherein the step of representing the nipple in the synthetic 2D image includes representing a clockwise position relative to the nipple of a selected pixel in the synthetic 2D image.

10. A method according to claim 7 further comprising the step of illustrating a cursor on the synthetic 2D image and the section of the 3D volumetric image on the display, wherein the cursor represents the location of the selected pixel in the synthetic 2D image and the corresponding position in the section of the 3D volumetric image.

11. A system for assisting a user in navigating through 2D and 3D image data to locate a region of interest within a breast tissue, the system comprising:
a 2D image acquisition system for acquiring 2D image data;
a 3D image acquisition system for acquiring 3D image data;
an analysis module operably connected to the 2D image acquisition system and the 3D image acquisition system and configured:
to generate a synthetic 2D image and a DBT volume from the acquired 2D image data;
to generate a 3D volume from the 3D image data;
to correlate locations within the DBT volume to locations within the 3D image volume;
to generate a navigation map providing information for locations of each pixel in the synthetic 2D image corresponding to a plane in the DBT volume and the 3D image volume; and
to select and present a section within the 3D volume corresponding to the navigation map information for a pixel selected within the synthetic 2D image;
a display operably connected to the analysis module and operable to display the synthetic 2D image and sections of the 3D volume; and
an input operably connected to the analysis module and configured to receive commands from a user regarding the selection of a pixel within the synthetic 2D image present on the display;
wherein the analysis module is further configured to generate the synthetic 2D image by:
detecting one or more volumes of interest (VOIs) within the 3D volumetric image;
determining the positions of the one or more VOIs from the 3D volumetric image within the DBT volume;
reprojecting the VOIs from the DBT volume; and modifying the navigation map to include the location of the VOIs.

12. A system according to claim 11 wherein the 3D image acquisition system is an automated breast ultrasound system (ABUS) or a magnetic resonance imaging (MRI) system.

13. A system according to claim 11 further comprising a computer aided detection system associated with the analysis module and configured with the analysis module to:
    detect regions of interest within the 3D volume;
    update the navigation map with the locations of the regions of interest (ROIs); and
    optionally enhance the synthetic 2D image to illustrate the ROIs.

14. A system according to claim 11 wherein the analysis module presents a cursor on the synthetic 2D image and the section of the 3D volume on the display, wherein the cursor represents the location of the selected pixel in the synthetic 2D image and the section of the 3D volume.

15. A system for assisting a user in navigating through 2D and 3D image data to locate a region of interest within a breast tissue, the system comprising:
    a 2D image acquisition system for acquiring 2D image data;
    a 3D image acquisition system for acquiring 3D image data;
    an analysis module operably connected to the 2D image acquisition system and the 3D image acquisition system and configured:
        to generate a synthetic 2D image and a DBT volume from the acquired 2D image data;
        to generate a 3D volume from the 3D image data;
        to correlate locations within the DBT volume to locations within the 3D image volume;
        to generate a navigation map providing information for each pixel in the synthetic 2D image corresponding to a plane in the DBT volume and the 3D image volume; and
        to select and present a section within the 3D volume corresponding to the navigation map information for a pixel selected within the synthetic 2D image;
    a display operably connected to the analysis module and operable to display the synthetic 2D image and sections of the 3D volume; and
    an input operably connected to the analysis module and configured to receive commands from a user regarding the selection of a pixel within the synthetic 2D image present on the display,
    wherein the analysis module is further configured to:
        detect a position of the nipple within the 3D volume;
        locating the position of the nipple from the 3D volume into the DBT volume; and
        represent the nipple and information on the location of the selected pixel relative to the nipple on the display in the synthetic 2D image formed from DBT volume and in the section of the 3D volume.

* * * * *